(12) United States Patent
Sutton et al.

(10) Patent No.: US 6,737,022 B1
(45) Date of Patent: May 18, 2004

(54) FRAGMENT COLLECTOR APPARATUS

(75) Inventors: John E. Sutton, Bellevue, NE (US); Donn H. Vanden Bosch, Omaha, NE (US)

(73) Assignee: Transgenomic, Inc., Omaha, NE (US)

( * ) Notice: Subject to any disclaimer, the term of this patent is extended or adjusted under 35 U.S.C. 154(b) by 0 days.

(21) Appl. No.: 09/557,854

(22) Filed: Apr. 26, 2000

Related U.S. Application Data

(63) Continuation-in-part of application No. 09/143,456, filed on Aug. 28, 1998, now Pat. No. 6,074,880.

(51) Int. Cl.[7] .................................................. G01N 1/14
(52) U.S. Cl. ................. 422/70; 73/61.43; 73/61.52; 73/61.59; 222/630; 222/637; 422/63; 422/81; 422/100; 436/52; 436/161; 436/174; 436/180
(58) Field of Search ................... 436/43, 50, 52–53, 436/161, 174, 180; 422/63, 70, 81, 100, 103; 73/61.43, 61.52, 61.59, 161, 56; 222/630, 637; 210/656, 215

(56) References Cited

U.S. PATENT DOCUMENTS

| | | | |
|---|---|---|---|
| 3,765,461 A | 10/1973 | Keck | 141/234 |
| 4,066,409 A | 1/1978 | Fine | 422/70 |
| 4,491,011 A | 1/1985 | Nordmeyer et al. | 73/61.1 C |
| 4,497,199 A | 2/1985 | Matson | 73/63.1 C |
| 5,310,463 A | 5/1994 | Dadoo et al. | 204/180.1 |
| 5,345,029 A * | 9/1994 | Schubert | 208/310 R |
| 5,389,221 A | 2/1995 | Jorgenson et al. | 204/299 R |
| 5,391,499 A | 2/1995 | Karkantis et al. | 436/180 |
| 5,520,817 A | 5/1996 | Anahara | 210/656 |
| 5,565,622 A | 10/1996 | Murphy | 73/61.55 |
| 5,585,236 A | 12/1996 | Bonn et al. | |
| 5,593,564 A | 1/1997 | Templin et al. | 204/451 |
| 5,670,054 A * | 9/1997 | Kibbey et al. | 210/143 |
| 5,772,889 A | 6/1998 | Gjerde et al. | |
| 5,872,010 A | 2/1999 | Karger et al. | 436/173 |
| 5,898,175 A | 4/1999 | Hirabayashi et al. | 250/288 |
| 5,917,184 A | 6/1999 | Carson et al. | 250/288 |
| 5,976,336 A | 11/1999 | Dubrow et al. | 204/453 |
| 6,066,258 A | 5/2000 | Gjerde et al. | |
| 6,401,769 B1 * | 6/2002 | Backes et al. | 141/31 |

FOREIGN PATENT DOCUMENTS

| | | |
|---|---|---|
| DE | 43 03 275 A1 | 2/1993 |
| EP | 0 691 148 A2 | 1/1996 |
| FR | 2 250 983 | 11/1974 |
| WO | WO 94/11305 | 5/1994 |
| WO | WO 98/56797 | 12/1998 |

OTHER PUBLICATIONS

XP 3000 Modular Digital Pump Operator's Manual, Cavaro Scientific Instruments, Inc., Aug. 1998.

* cited by examiner

Primary Examiner—Arlen Soderquist
(74) Attorney, Agent, or Firm—Licata & Tyrrell P.C.

(57) ABSTRACT

A system for separating an aqueous stream of mixed polynucleotides into a series of length-based polynucleotide fractions and collecting one or more of the length-based polynucleotide fractions into separate containers. The system comprises a separation column containing separation media for separating an aqueous stream of mixed polynucleotides into a series of length-based polynucleotide fractions; a container including one or more single-sample containers; an ejection chamber having a separated sample inlet for receiving the length-based polynucleotide fractions, a waste outlet for discharging uncollected sample, and a capillary-sized fraction outlet positioned to discharge a selected length-based polynucleotide fraction into a single-sample container. The system also includes means for effecting discharge of a selected length-based polynucleotide fraction into the separate container. The means for effecting discharge of a selected length-based polynucleotide fraction into a separate container can include a puff valve having a pressurized gas inlet and a puff gas outlet and the ejection chamber can include a puff gas inlet communicating with the puff gas outlet, whereby activation of the puff valve will discharge a puff of gas into the ejection chamber and will effect discharge of sample through the fraction outlet; or the means can include a flow restriction actuator and flow restriction to increase liquid pressure in the ejection chamber. Computer controls and a method for fraction collection are also described.

14 Claims, 12 Drawing Sheets

FIG.—1

FRAGMENT COLLECTOR APPARATUS

CROSS-REFERENCE TO RELATED APPLICATION

This application is a continuation-in-part of commonly assigned U.S. patent application Ser. No. 09/143,456 filed Aug. 28, 1998 (now U.S. Pat. No. 6,074,880).

FIELD OF THE INVENTION

This invention relates to fraction collection of sample analyte containing solutions. More particularly the present invention is a system and method which allows user controlled formation and ejection of small volume droplets or streams of sample analyte containing solutions, thereby enabling precise user directed fractionalization and distributed collection of sample analyte(s).

BACKGROUND

Chromatographic separation systems for separating fractions of double-stranded DNA (dsDNA), single-stranded DNA (ssDNA), oligonucleotides, RNA and the like by chromatography have relied upon collection carousels to collect the samples. In one conventional system, a carousel positions collection vials, one after the other, under the outlet of the separation equipment for a specified length of time.

A new chromatographic separation process, Matched Ion Pair Chromatography (MIPC), has presented a separation process which can separate dsDNA into base-length sized fractions with an unprecedented precision. Each base-pair length is eluted in a predictable and calculable solvent concentration, permitting a user to precisely predict the specific time when a fraction having a particular base-pair length will be delivered from the bottom opening of the separation column. A new chromatographic separation system described in Provisional Application Serial No. 60/119,936 filed Feb. 12, 1999 and applications cited therein, has been constructed to apply the MIPC separation technology. To make full use of this new technology, eluant from the separation column containing a specific target fraction or fractions must be collected, unmixed, in separate identified vials. The prior art collection systems are unable to satisfy this need.

A most common chromatography eluant collection system uses a circular carousel with a circular array of receptors which contain sample collection vials. Modern biochemical procedures involve simultaneous processing a large number of samples, and rectangular multiwell or microtiter plates or trays with 96, 384 and 1536 sample well or vial configurations with standardized dimensions and X-axis and Y-axis positioning of each well are in common use. It is desirable to collect fractions from the MIPC separation systems directly into designated respective vials or wells in these collection plates. The traditional systems are unable to satisfy this need.

Two-way valves are used in many systems to redirect liquid flow to a by-pass or shunt. However, valves of this type are unsatisfactory for diverting the fractions into collecting vials because they introduce "dead-volume" which degrades the separation between fractions and causes contamination from one fraction to the next.

Prior art systems also produce droplets having a volume which may be so large as to include more than the segment to be collected. Reducing droplet size by using a smaller outlet orifice can introduce shear forces which can disrupt or break larger polynucleotides.

SUMMARY OF THE INVENTION

One object of this invention is an apparatus and method for collecting with precision an eluant fraction from a chromatographic column into a designated collection vial at a predetermined time.

It is a further object of this invention to provide an apparatus and method for collecting with precision eluant fractions from a chromatographic column into designated vials of a multiwell plate.

It is a still further object of this invention to provide a system for enabling a drop-by-drop ejection of sample analyte containing solution from a contained flow stream thereof into a collection vial with small volumes and without subjecting the liquid to destructive shear forces.

It is another object of this invention to provide a system for separating an aqueous stream of mixed polynucleotides into a series of length-based polynucleotide fractions and collecting one or more of the length-based polynucleotide fractions into separate containers. The system comprises a separation column containing separation media for separating an aqueous stream of mixed polynucleotides into a series of length-based polynucleotide fractions; a container including one or more single-sample vials or wells; an ejection chamber having a separated sample inlet for receiving the length-based polynucleotide fractions, a waste outlet for discharging uncollected sample, and a capillary-sized fraction outlet positioned to discharge a selected length-based polynucleotide fraction into a single-sample container. The system also includes means for effecting discharge of a selected length-based polynucleotide fraction into the separate container.

The means for effecting discharge of a selected length-based polynucleotide fraction into a separate container can include a puff valve having a pressurized gas inlet and a puff gas outlet and the ejection chamber can include a puff gas inlet communicating with the puff gas outlet, whereby activation of the puff valve will discharge a puff of gas into the ejection chamber and will effect discharge of liquid sample through the fraction outlet.

The means for effecting discharge of a selected length-based polynucleotide liquid fraction into a separate container can include a flow restriction actuator, a flow restriction in the waste conduit which will restrict flow of uncollected sample upon actuation by the flow restriction actuator, whereby actuation of the flow restriction will effect an increase in liquid pressure in the ejection chamber. Actuation of the flow restriction can effect discharge of sample through the fraction outlet. The system preferably includes computer control means for effecting discharge of the length-based polynucleotide fractions by actuation of the flow restriction. This can be combined with a puff valve having a pressurized gas inlet and a puff gas outlet wherein the ejection chamber includes a puff gas inlet communicating with the puff gas outlet, whereby activation of the puff valve will discharge a puff of gas into the ejection chamber and will effect discharge of sample through the fraction outlet. In this combination, the computer control means can effect discharge of the length-based polynucleotide fractions by opening the air-puff valve.

The fraction outlet has an outlet opening, and the outlet opening can be combined with drop size reduction means for reducing the size of droplets discharged into the sample container. The drop size reduction means can be a gas-knife surrounding the fraction outlet and positioned to dislodge fluid through the outlet opening in the form of small droplets; a piezo-electric vibrator, or an electrostatic separator, or a combination thereof. The drop size reduction means can include a nozzle having a small orifice wherein the gas-knife surrounds the nozzle and is positioned to dislodge fluid through the outlet opening in the form of small droplets; the drop size reduction means can be a piezo-electric vibrator positioned adjacent to the nozzle; or the drop size reduction means can be an electrostatic separator, and the nozzle having a charge opposite to the charge of the sample container.

The system of this invention can include computer control means for controlling the means for effecting discharge of the length-based polynucleotide fractions. The computer control means can include means for responding to a fraction detector output signal to determine the time interval for effecting discharge of a length-base fraction, means for responding to a fraction detector output signal to determine when the signal strength exceeds a threshold value to determine the time interval for effecting discharge of a length-base fraction, or means for responding to a fraction detector output signal to determine when the signal slope exceeds a preset value to determine the time for beginning discharge of a length-base fraction.

The method of this invention includes separating an aqueous stream of mixed polynucleotides into a series of length-based polynucleotide fractions and collecting one or more of the length-based polynucleotide fractions into separate single-fraction containers with a system comprising a chromatographic separation system for separating a mixture of polynucleotides into size-based fractions in an eluant stream; an ejection chamber having a separated sample inlet for receiving the length-based polynucleotide fractions, a waste outlet for discharging uncollected sample, and a fraction outlet positioned to discharge a selected length-based polynucleotide fraction into a single-sample container; and means for effecting discharge of a selected length-based polynucleotide fraction into the single-sample container. The method comprises the steps of (a) passing the eluant stream carrying successive, separated size-based fractions through the ejection chamber; (b) determining when a selected length-based polynucleotide fraction will pass through the ejection chamber; and (c) effecting discharge of a selected length-based polynucleotide fraction into a sample container.

In this method, the time interval within which a selected length-based polynucleotide fraction will pass through the ejection chamber is determined, and eluant in the ejection chamber during this time interval is discharged into the sample container. When the system includes a detector system between the separation system and the ejection chamber and the detector system produces an output signal which is a function of the concentration of a fraction in the eluant stream, step (b) can comprise determining when the output signal from the detector exceeds a preset threshold level indicating the presence of the selected fraction; or determining when the output signal from the detector exceeds a preset slope indicating the presence of the selected fraction.

DETAILED DESCRIPTION OF THE INVENTION

The apparatus of this invention provide a novel and unique method for separating and purifying single strand oligonucleotides and single stranded DNA fragments, double stranded DNA fragments, RNA, plasmids and the like. The device simplifies the separation procedure and applies a unique size-based separation process based on our Matched Ion Pair Chromatography (MIPC), also denoted herein by the term DNA Chromatography. This process exploits the binding characteristics of polynucleotides with non-polar surfaces of separation media in the presence of counter-ion. Materials in aqueous solutions of the counter-ion and low stripping solvent concentrations bind to the non-polar surfaces, and the materials are subsequently released from the surface by application of a stripping solvent concentration which removes or strips materials from the separation media surface, the size of the materials being stripped being a function of the stripping solvent concentration. Larger sized materials require application of a greater stripping solvent concentration to effect their release. The size stripped to stripping solvent concentration can be calibrated and is so repeatable that it can be calculated with high accuracy. The process can be applied with any system which can retain the separation media and provides means to rapidly pass liquids through the separation media. This system provides a major advance in the size-based separation and collection of single strand oligonucleotides and single stranded DNA fragments, double stranded DNA fragments, RNA, plasmids and the like.

Figure 1:
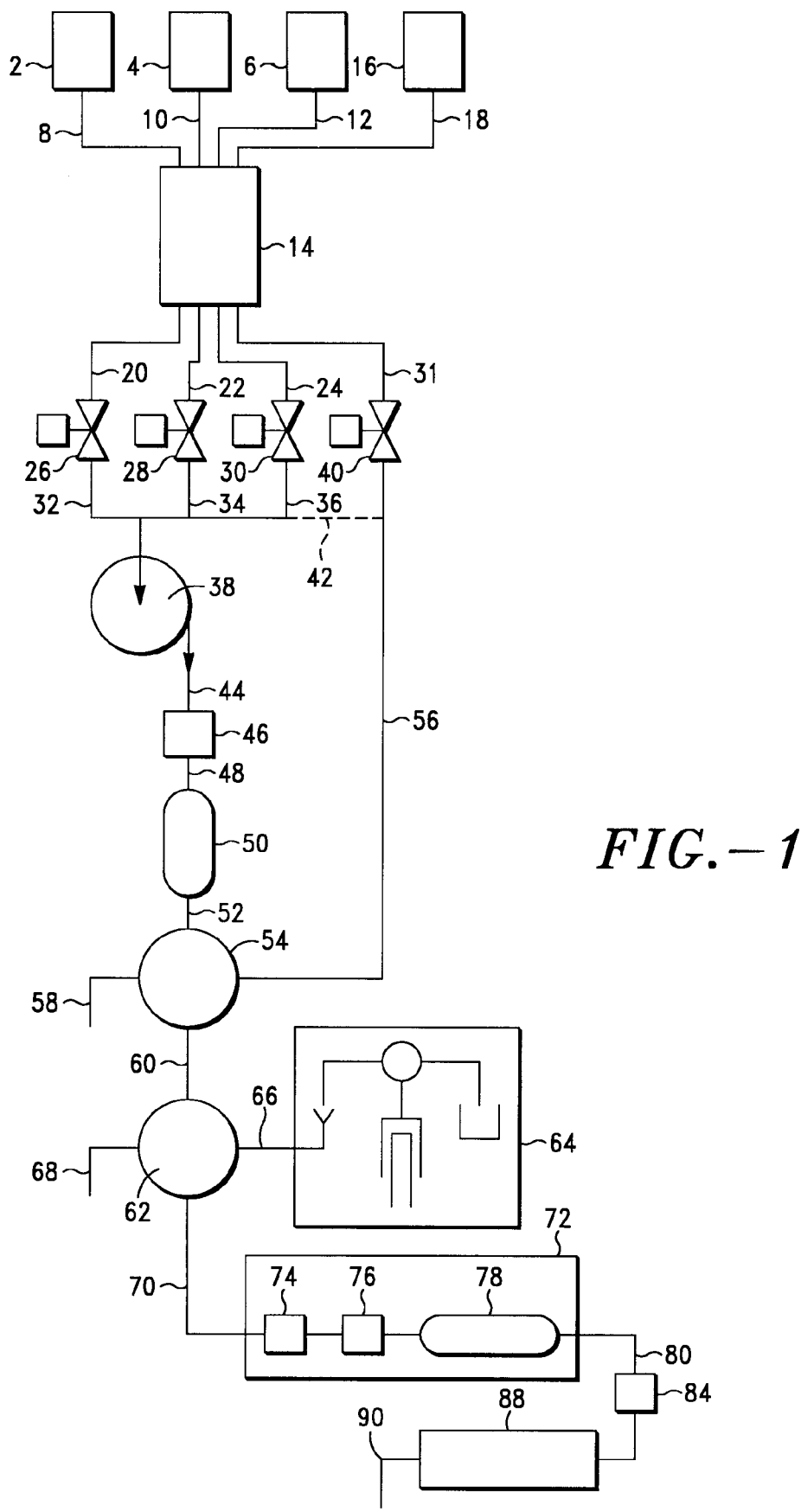
FIG. 1 is a schematic view, showing the relationship of the fragment collector to the separation system of this invention.

FIG. 1 is a schematic representation of a high pressure system for performing the matched ion pair chromatography (MIPC) method of this invention, with a proportioning valve system for effecting gradients of solvent concentrations in the separation. Chromatographic solutions such as solvents, counter-ions, and other solutions to be mixed with the solvents are maintained in solvent container 2, carrier liquid container 4, and auxiliary liquid (e.g., a co-solvent) container 6 having respective solvent transport tubing 8, carrier transport tubing 10 and auxiliary liquid transport tubing 12 communicating therewith and leading to degasser 14.

Column cleaning solution is contained in cleaning solution container 16 which likewise has a cleaning solution transport conduit 18 communicating therewith leading to the degasser 14. In this embodiment, the cleaning solution can flow by gravity pressure if the container 16 is elevated above the degasser and injection valve 54.

Degassed solvent conduit 20, degassed carrier liquid conduit 22, and degassed auxiliary liquid conduit 24 leading from the degasser 14 communicate with respective solvent proportioning valve 26, carrier liquid proportioning valve 28, and auxiliary liquid proportioning valve 30. The settings for these proportioning valves are set and changed by valve operators such as stepper motors associated therewith, and these valve operators respond to establish a desired set of settings in response to commands from the valve operator control module described in greater detail hereinafter. The settings for these proportioning valves control the ratio of liquids (co-solvents, driving solvents, etc.) through the injector valve and the separation column. Conduits 32, 34, and 36 lead from respective proportioning valves 26, 28 and 30 to the intake of the pump 38. The degasser 14 removes dissolved gases from the liquids. Removal of dissolved oxygen is particularly important because its presence increases the risk of oxidizing ferrous or other oxidizable metals in the system components and thus introducing the corresponding cations into the liquid.

The cleaning solution transport conduit 31 leads to a cleaning solution valve 40. An optional cleaning solution conduit 42 leads from the valve 40 and communicates with the inlet of the pump 38.

The openings of valves 26, 28 and 30 accurately set the relative ratios of the solvent or solvents to carrier liquid, a most important part of this system because the size-based DNA separation by MIPC is a function of solvent concentration. As will be described with regard to the various DNA fragment separation processes, the slope of the solvent gradient as a function of time is changed during the separation process, and the most critical phase may require a very precise gradient, or for some processes, a highly precise isocratic (constant solvent concentration) composition. The settings of the valves 26, 28 and 30 are established by conventional valve actuators which can be remotely set by signals to a conventional valve control device. The control system of this invention provides computer controlled instructions which establish the settings of valves 26, 28 and 30 to precise flow values at appropriate times during the operation of the system.

In a similar manner, the control system of this invention provides computer controlled instructions to establish the operational parameters of the pump 38, such as the off/on status of the pump and the pressure or flow rate settings of the pump.

Pump outflow conduit 44 communicates with the in-line mixer 46, directing the liquid flow through the mixer 46 for thorough mixing of the components. Mixed liquid outflow conduit 48 communicates with guard column 50 to treat the mixed liquid to remove multivalent metal cations and other contaminants which would interfere with the separation of DNA fragments. Guard column 50 can contain a cation exchange resin in sodium or hydrogen form for removal of multivalent metal cations by conventional ion exchange. Conduit 52 communicates with the outlet of the guard column and an inlet port of a cleaning solution injector valve 54. Cleaning solution supply conduit 56 connects valve 40 with the cleaning solution injector valve 54, and waste outlet conduit 58 leads to waste. Conduit 60 leads from the cleaning solution injector valve 54 to the sample injection valve 62.

Sample aliquot selector 64 communicates with injector valve 62 through sample conduit 66. Waste conduit 68 leads from the injector valve and removes waste liquids.

In the injector valve 62, the sample is introduced into a stream of solvent and carrier liquid passing through the valve from conduit 60. Sample conduit 70 communicates with an outlet port of injector valve 62 and with the column prefilter 74 in the air bath oven 72. The capillary tubing coil 76 communicates with the prefilter 74 and the inlet of separation column 78. The extended length of the capillary coil 76 allows ample heat to pass from the heated oven air into the liquid passing through the coil, bringing the liquid within $\pm 0.05°$ C. of a selected temperature. The oven 72 establishes this temperature uniformity in the prefilter 74, coil 76, and separation column 78.

The separation column 78 is packed in a conventional column construction with beads having a unique separation surface which effects a size-based separation of DNA fragments in the presence of a matched counter-ion by the MICP process. A stream (eluant) containing base pair length size-separated DNA fragments passes from the separation column 78 through eluant conduit 80.

Analyzer conduit 80 communicates with an analyzer cell 84. The analyzer cell can be a convention UV emission measurement device which measures the UV emission level of the native DNA fragment structures in the liquid. The emission level is a function of the concentration of the DNA fragments in the liquid being tested.

Alternatively, if the DNA can be labeled with a fluorescent marker, the analyzer continuously measuring the level of the fluorescent marker in the liquid by detecting the emission level at the frequency most appropriate for the marker. It will be readily apparent that any analyzing system capable of continuously measuring a characteristic of the liquid which is a function of the concentration of the DNA fragments therein is suitable and intended to be within the scope of this invention.

The eluant passes from the analyzer 84 to the fragment collector 88. In the fragment collector 88, selected portions of the eluant containing a separated DNA fraction are collected in a vials for later processing or analysis. Uncollected fractions are removed through waste conduit 90.

The DNA separation process is impaired by the presence of multivalent cations. In the above description, the liquid flow system is described as a series of conduits. The conduits are capillary tubing selected to avoid introduction of multivalent cations into the liquids. The preferred capillary tubing materials are titanium and PEEK. For similar reasons, the other components of the system are preferably made of titanium or PEEK or have the surfaces exposed to the liquid coated with PEEK to protect them from oxidation and prevent the introduction of multivalent cations into the liquid.

Stainless steel can also be used provided it has been treated to remove all oxidized surface materials and the solutions contacting the stainless steel surfaces are free of dissolved oxygen.

Figure 2:
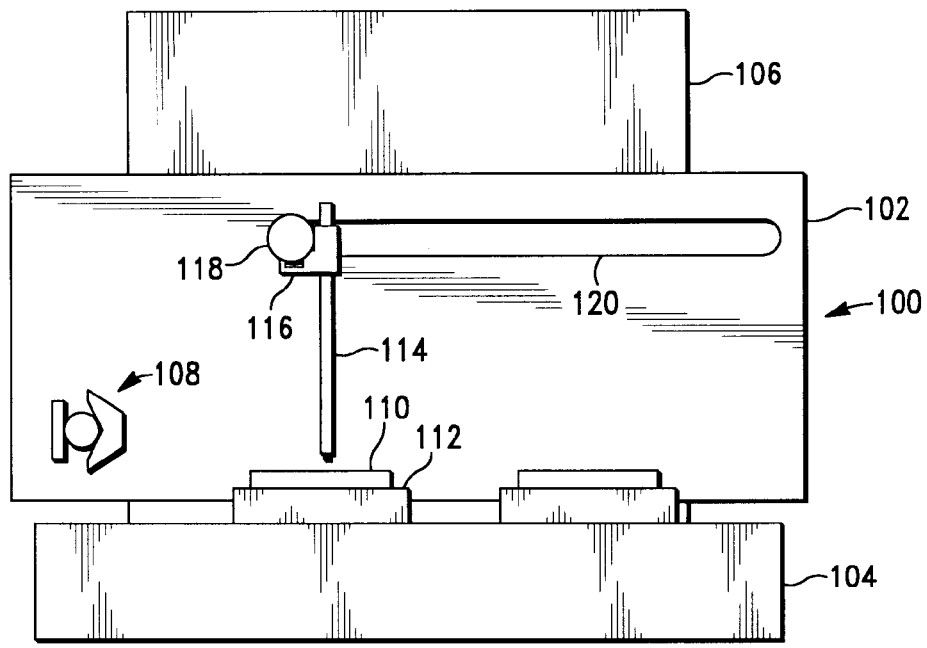
FIG. 2 is a front view of the fragment collector of this invention.
Figure 3:
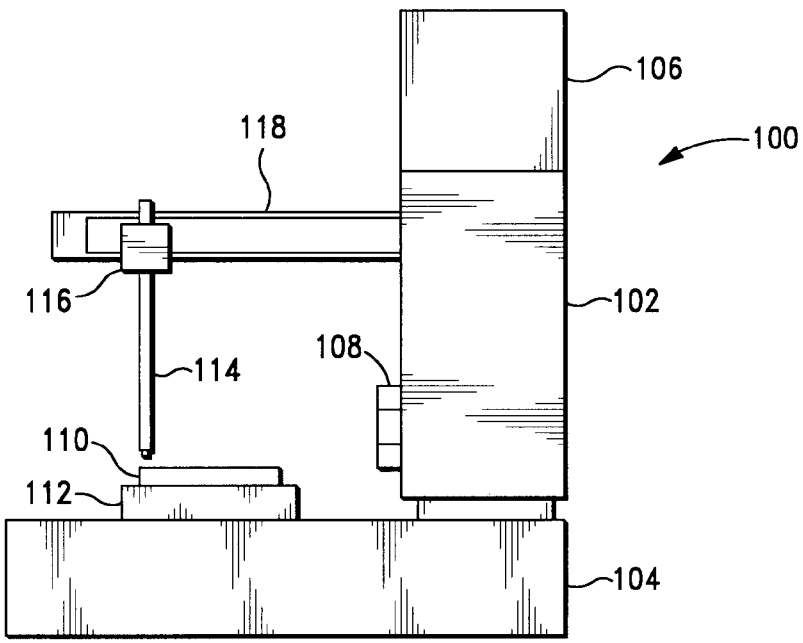
FIG. 3 is an end view of the fragment collector shown in FIG. 2.

FIG. 2 is a front view of the fragment collector of this invention, and FIG. 3 is an end view of the fragment collector show in FIG. 2, illustrating details of the X-axis movement control system 122. The fragment collector 100 has a controller housing 102, a sample tray support 104 and a puff controller housing 106. A pinch valve 108 is mounted on the front of the controller housing 102 for terminating flow of fluid. The multiwell plates 110 are supported on Peltier cooled chill pads 112. A fragment dispenser 114 is supported on dispenser support carriage 116. The dispenser support carriage 116 is supported for Y-axis movement on the Y-axis movement controller 118. The Y-axis movement controller 118 extends through slot 120 to an X-axis movement control system 122 shown in FIG. 4.

The X-axis and Y-axis movement control systems move the dispenser support 116 to a X-Y coordinate corresponding to the central axis of a well in plate 110 into which a fraction is to be dispensed, maintain the dispenser in this position until the fraction is dispensed and them move the dispenser to the X-Y coordinate corresponding to the central axis of the next well into which a fraction is to be dispensed.

Figure 4:
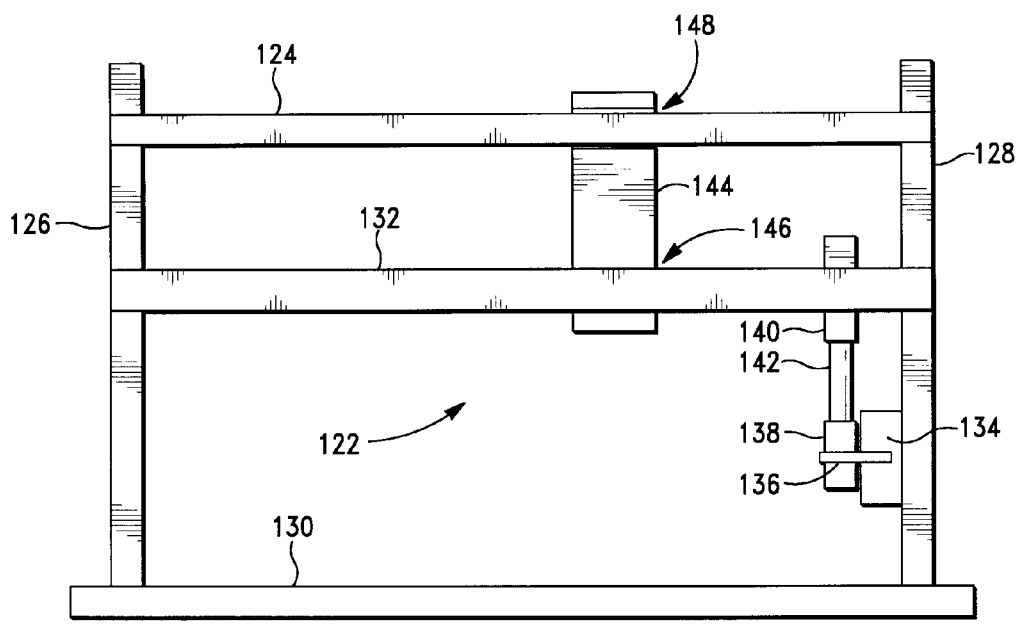
FIG. 4 is a partial front view of the fragment collector of FIG. 2 with a front panel removed to show details of the worm gear drive assembly for X-axis movement of the fragment dispenser.

FIG. 4 is a partial front view of the fragment collector of FIG. 2 with a front panel removed to show details of the worm gear drive assembly for X-axis movement of the fragment dispenser. A guide rod 124 is supported at its ends by the left and right support panels 126 and 128. Support panels 126 and 128 are mounted on horizontal support plate 130. An externally threaded worm gear 132 is mounted for rotation about its central axis on conventional bearings (not shown) supported on the left and right support panels 126 and 128. Stepper motor 134, mounted on the right support panel 128, has an axle 136 upon which a first drive pulley 138 is mounted. A second drive pulley 140 is mounted on the worm gear 132 in a position aligned with the first drive pulley 138. Drive belt 142 engages pulleys 138 and 140 to translate rotary motion of the motor axle 136 to the worm gear 132.

Figures 5, 6:
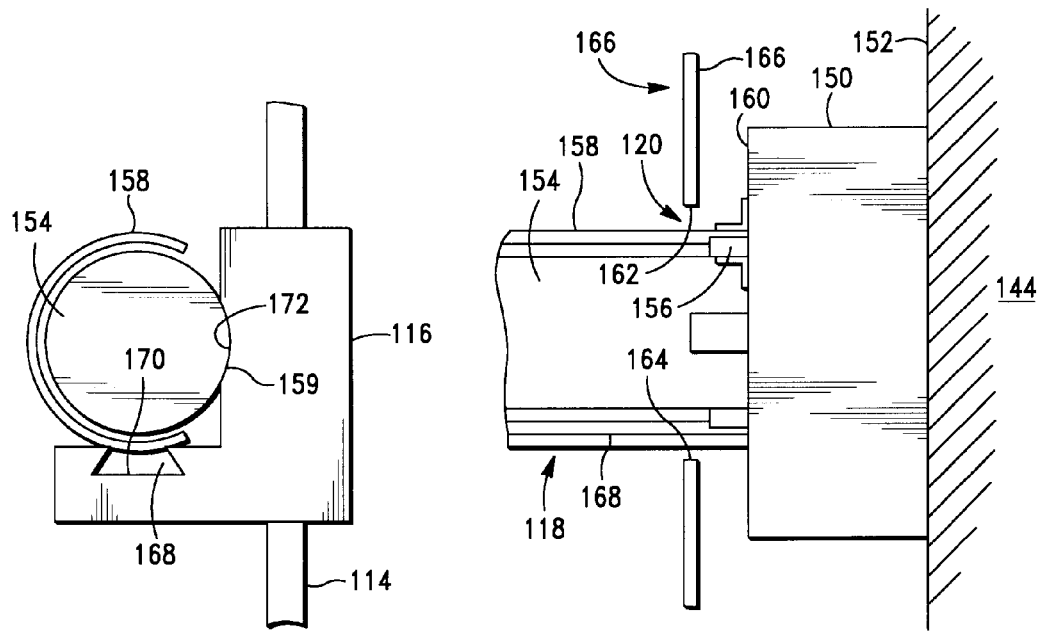
FIG. 5 is a fragmentary view of the motor and worm gear assembly of the drive assembly for Y-axis movement of the fragment dispenser.
FIG. 6 is an end view of the drive assembly for Y-axis movement of the fragment dispenser.

The Y-axis movement controller 118 is supported on the X-axis movement carriage 144 (FIG. 5). The X-axis movement carriage 144 has an internally threaded bore 146 which engages the external threads of the worm gear 132. A channel 148 in the X-axis movement carriage 144 is positioned for sliding engagement with the guide rod 124 for sliding movement in the X-axis direction. The guide rod 124 stabilizes the X-axis movement carriage against rotation about the axis of the worm gear 132 when the worm gear turns.

Stepped activation of the stepper motor 134 is translated to a stepped rotation of the worm gear 132, moving the X-axis movement carriage to the left or right along the X-axis to a position which places the dispenser in alignment with the X-axis coordinate of a well into which a fraction is to be dispensed.

FIG. 5 is a fragmentary view of the motor and worm gear assembly of the drive assembly for Y-axis movement of the fragment dispenser. A Y-axis stepper motor 150 is supported on a support surface 152 of the X-axis movement carriage 144. A Y-axis worm gear 154 is mounted on the stepper motor drive 156. The Y-axis worm gear 154 is partially enclosed in an outer sheath 158. The outer sheath 158 can be mounted on the surface 160 of the housing of the stepper motor 150 or alternatively, it can be attached to the carriage 144. The slot 120 is defined by opposed edges 162 and 164 of the front panel 166.

A guide 168 is mounted on the undersurface of the sheath 158 in an axially parallel alignment with the sheath 158 and the worm gear 154.

FIG. 6 is an end view of the drive assembly shown in FIGS. 4 and 5. This shows further details of the drive assembly for Y-axis movement of the fragment dispenser. The sheath 158 has a lateral opening which exposes the threaded engaging surfaces 159 of the worm gear 154. The dispenser support 116 is supported by mutual engagement of the guide 168 and a matched dispenser support groove 170. The inwardly sloped edges of the guide 168 engage the correspondingly outwardly sloped opposed edges of the support groove 170. The dispenser support 116 has a grooved surface 172 which engages the engaging surfaces 159 of the worm gear 154.

Rotation of the worm gear 154 effects a Y-axis movement of the dispenser support 116. The groove 170 engagement with the guide 168 stabilizes the dispenser support 116 against rotary movement about the axis of the worm gear 154 when it rotates. Stepped activation of the stepper motor 150 is translated to a stepped rotation of the work gear 154, moving the dispenser support 116 to the backward or forward along the Y-axis to a position which places the dispenser in alignment with the Y-axis coordinate of a well into which a fraction is to be dispensed.

It will be readily apparent to a person skilled in the art that the matched engaging surfaces of the guide 168 and the groove 170 can be other arrangements which provide the guide and stabilizing function of the guide and groove engagement.

Figure 7:
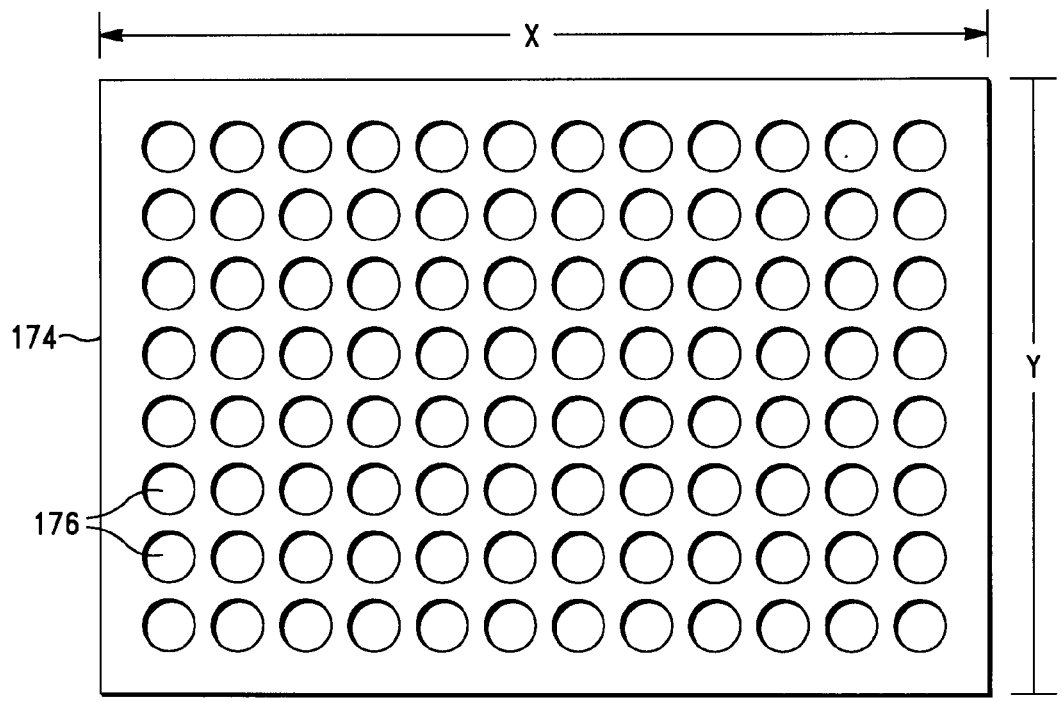
FIG. 7 is a top view of a standard 96 well multiwell plate.

FIG. 7 is a top view of a standard 96 well multiwell plate or microtiter plate. The microtiter plate 174 has sample wells 176, the center axis of each well having exact repeated spacings along the X and Y axes from the central axes of next adjacent wells. The number of wells and the well spacings can be selected to have any value desired. The shape, size and distribution of wells have been standardized for 96, 384, and 1536 well microtiter plates, for example, and each or all of these can be used in conjunction with the fragment collector of this invention. The wells can be used as shown or they can be protected from sample contamination by receive individual sample vial liners or a conventional overlay plate liner containing sample vials which have outer dimensions corresponding to the inner dimensions of the microtiter plate wells.

Figure 8:
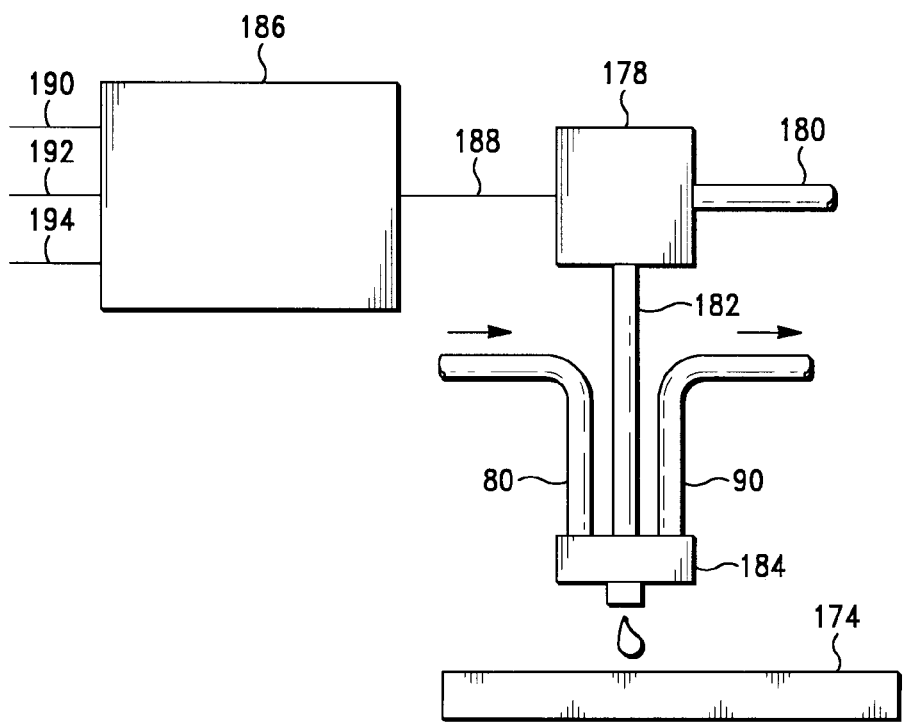
FIG. 8 is a schematic view of an air-puff dispenser embodiment of this invention.

FIG. 8 is a schematic view of an air-puff dispenser embodiment of this invention. Features of this system are described in copending, commonly assigned U.S. patent application Ser. No. 09/143,456 filed Aug. 28, 1998, the entire contents of which are hereby incorporated by reference. Pressurized gas is fed to the puff valve 178 through conduit 180 from a source of pressurized gas (not shown). Conduit 182 communicates with the puff valve 178 and with the sample dispenser 184. Conduit 80 communicates with the separation system shown in FIG. 1 and with the dispenser 184. The puff valve 178 is connected with the fragment collector controller 186 by communication line 188 for receiving operating valve open and valve close signals from the controller. The valve open signal is given to the puff valve 178 when a sample is to be dispensed into a well or vial in the multiwell plate 174, and the valve closed signal is given to the puff valve 178 when the sample collection is completed or when the vial is full, whichever is earlier. The collection controller 186 provides the valve open and valve closed signals in response to data and instructions received through communication lines 190, 192 and 194, for example.

Figure 9:
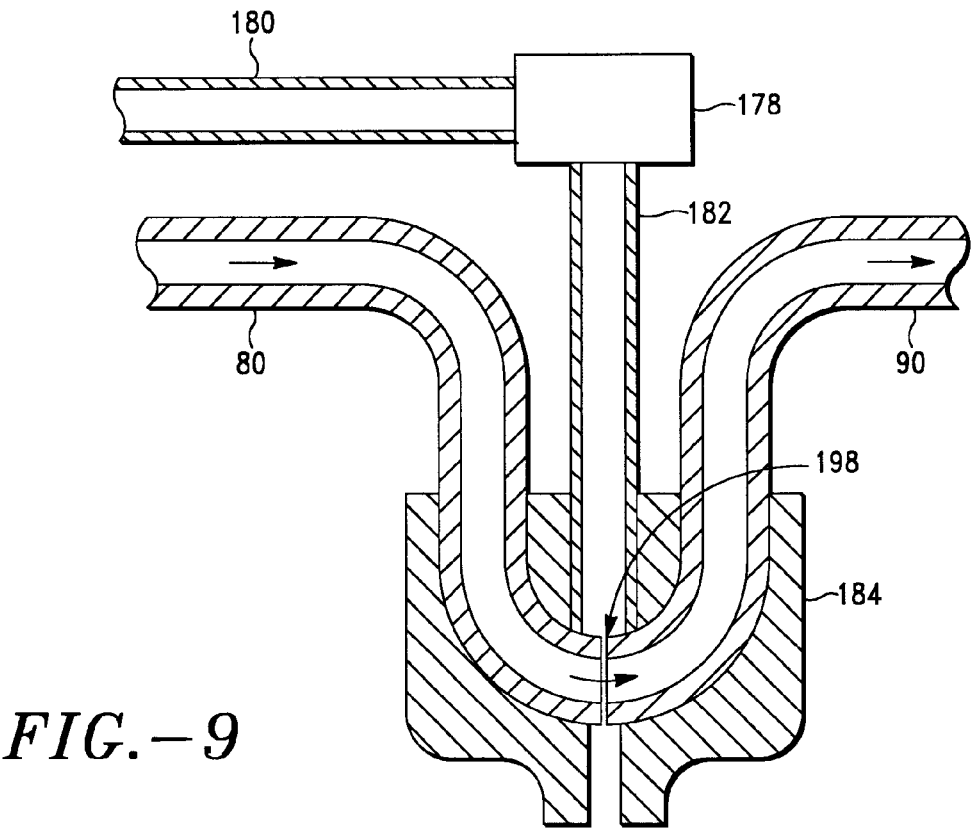
FIG. 9 is an enlarged cross-sectional view of the air-puff dispenser embodiment of FIG. 8.

FIG. 9 is an enlarged cross-sectional view of the air-puff dispenser embodiment of FIG. 8 showing the elements thereof when the puff valve 178 is in a closed position. The sample supply conduit 80 passes through the dispenser 184 and becomes conduit 90 to waste. A pin hole or small pass capillary passageway 198 through the conduit 80 communicates with the air puff conduit 182 through an opening in the passageway. When the puff valve 178 is closed, sample fluid passes through the conduit 80 to the waste conduit 90 without interruption. The capillary hole or passageway 80 has a capillary size, so fluid in this passageway is stationary when the puff valve 178 is closed.

Figure 10:
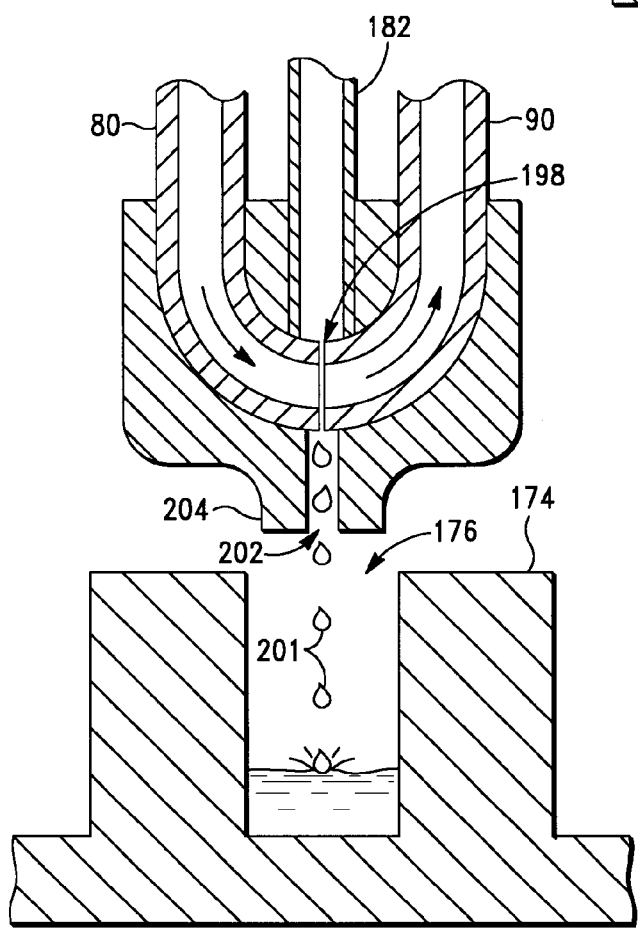
FIG. 10 is an enlarged cross-sectional fragmentary view of the dispenser tip and well of a multiwell plate show in FIG. 9.

FIG. 10 is an enlarged cross-sectional fragmentary view of the dispenser tip shown in FIG. 9 when the puff valve 178 is opened to expel a droplet of sample into a well of the multiwell plate. In this view, the sample continues to flow through inlet conduit 80. When the puff valve 178 is opened, a puff of air passes through the conduit 182 through capillary passageway or pin hole 198 and expelling one or more drops of liquid 201 from the tip 204 of the passageway 202 into well 176. The puff valve 178 can be opened and closed to create a quick succession of bursts, expelling a series of drops into the well 176 until either the sample collection is complete or the well 176 is filled.

Figure 11:
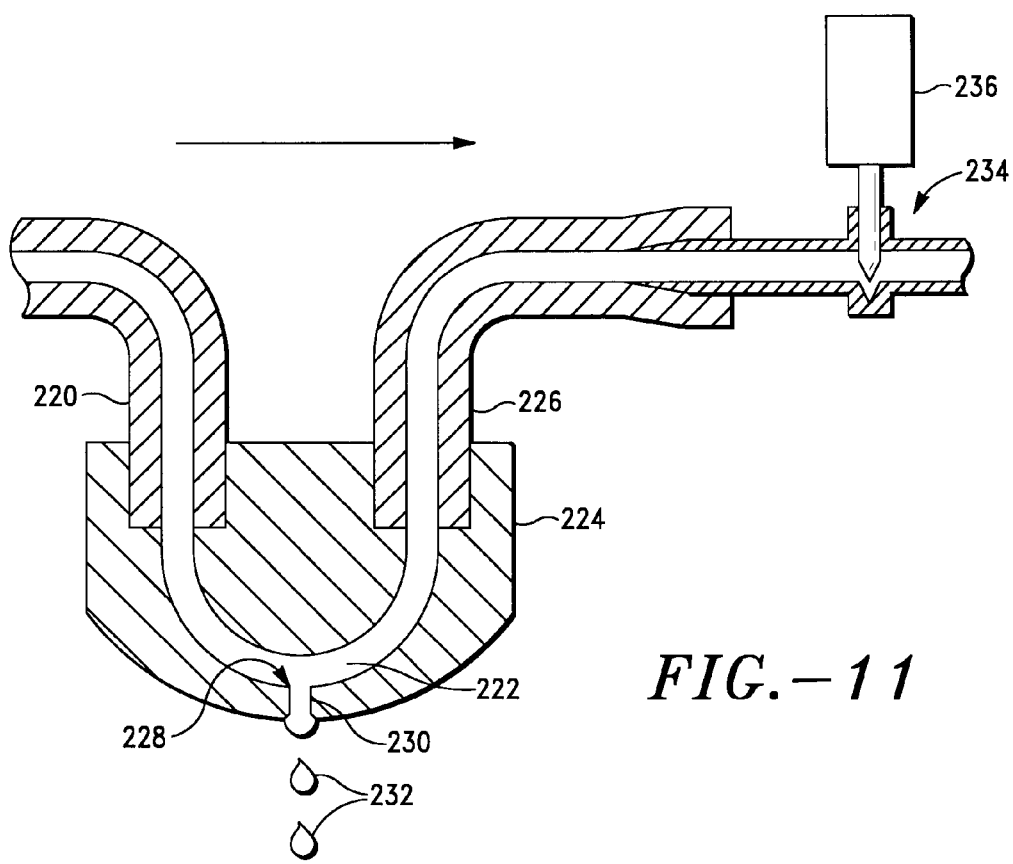
FIG. 11 is a cross-sectional view of an alternate embodiment of a dispenser tip according to this invention with a flow restriction in the outlet line.

FIG. 11 is a cross-sectional view of an alternate embodiment of a dispenser tip according to this invention with a flow restriction in the outlet line. The eluant inlet conduit 220 through which the eluant containing the sample fractions leads to an ejection chamber 222 in the ejector tip 224. The ejection chamber 222 communicates with an outlet waste conduit 226 and a droplet ejection port 228 with a capillary-size droplet forming opening 230. Droplets 232 falling from the opening 230 are collected in a sample vial (not shown). A flow restriction 234 having a restriction actuator 236 is positioned in the outlet conduit 226. The restriction actuator can be a conventional solenoid. A signal voltage to the restriction actuator 236 and restriction 234 can be constructed to provide the desired degree of restriction in flow through the conduit 226. It will be readily apparent to a person skilled in the art that the flow restriction can be achieved by any adjustable flow-through valve including pinch valves, gate valves and the like, and the invention is intended to cover the use of all adjustable restriction valves which provide the desired degree of restriction.

Figure 12:
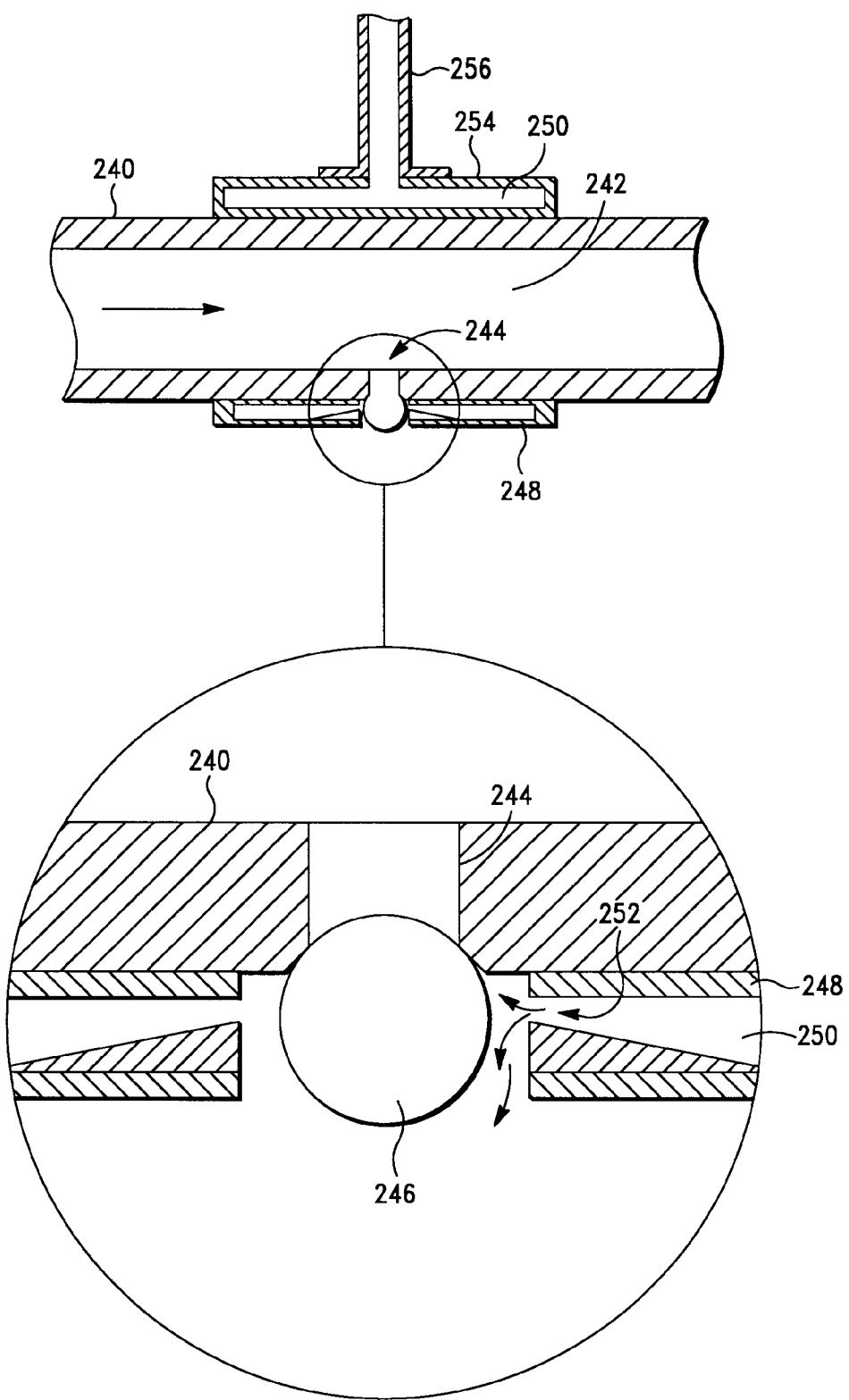
FIG. 12 is a cross-sectional view of an alternate dispenser tip with air knife drop size control with an expanded view of the dispenser.

FIG. 12 is a schematic cross-sectional view of an alternate dispenser tip with air knife drop size control and an expanded view of the dispenser tip. The eluant inlet conduit 240 through which the eluant containing the sample fractions flows, leads to an ejection chamber 242. Drop ejection outlet passageway 244 communicates with the ejection chamber 242 to form a droplet 246 in the outlet end thereof. A gas or air-knife 248 surrounds the outlet 244 directing a gas stream from the compressed gas distributor 250 through a narrow restriction 252 to form the planar air knife. The compressed gas is supplied to the air knife and distributor 250 through the cylindrical gas distributor 254 which, in turn, communicated with the compressed gas inlet conduit 256. The gas conduit 256 is provided with a conventional pressure controller (not shown) to adjust the gas pressure to the level which provides the desired droplet size.

Figure 13:
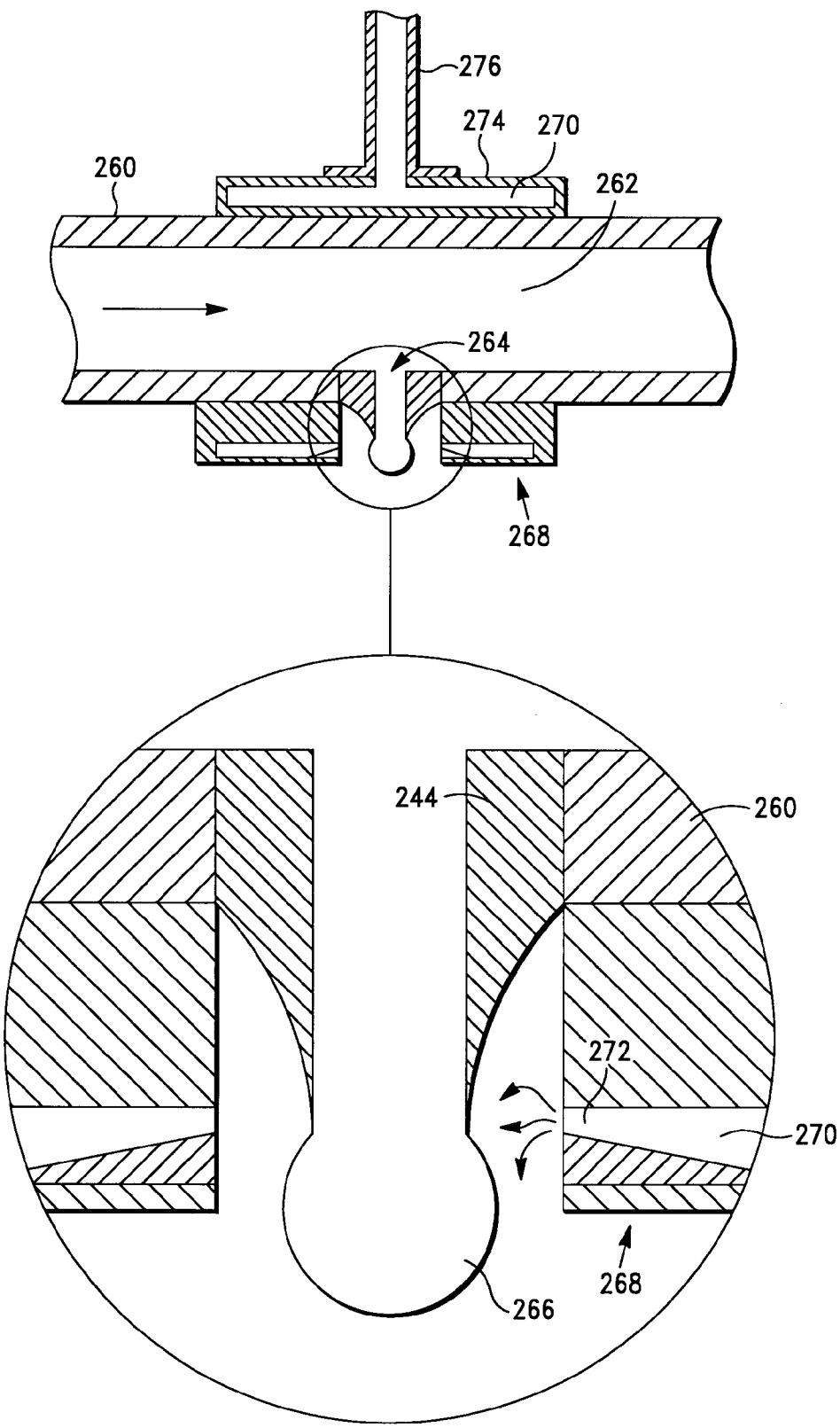
FIG. 13 is a cross-sectional view of an alternate dispenser tip with a nozzle and air knife drop combination for drop size control and an expanded view of the dispenser tip.

FIG. 13 is a schematic cross-sectional view of an alternate dispenser tip with a nozzle and air knife drop combination for drop size control and an expanded schematic cross-sectional view of the dispenser tip. The eluant inlet conduit 260 through which the eluant containing the sample fractions flows, leads to an ejection chamber 262. Drop ejection outlet passageway nozzle 264 communicates with the ejection chamber 262 to form a droplet 266 in the outlet end thereof. A gas or air-knife 268 surrounds the outlet 264 directing a gas stream from the compressed gas distributor 270 through a narrow restriction 272 to form the planar air knife. The compressed gas is supplied to the air knife and distributor 270 through the cylindrical gas distributor 274 which, in turn, communicated with the compressed gas inlet conduit 276. The gas conduit 276 is provided with a conventional pressure controller (not shown) to adjust the gas pressure to the level which provides the desired droplet size.

Figure 14:
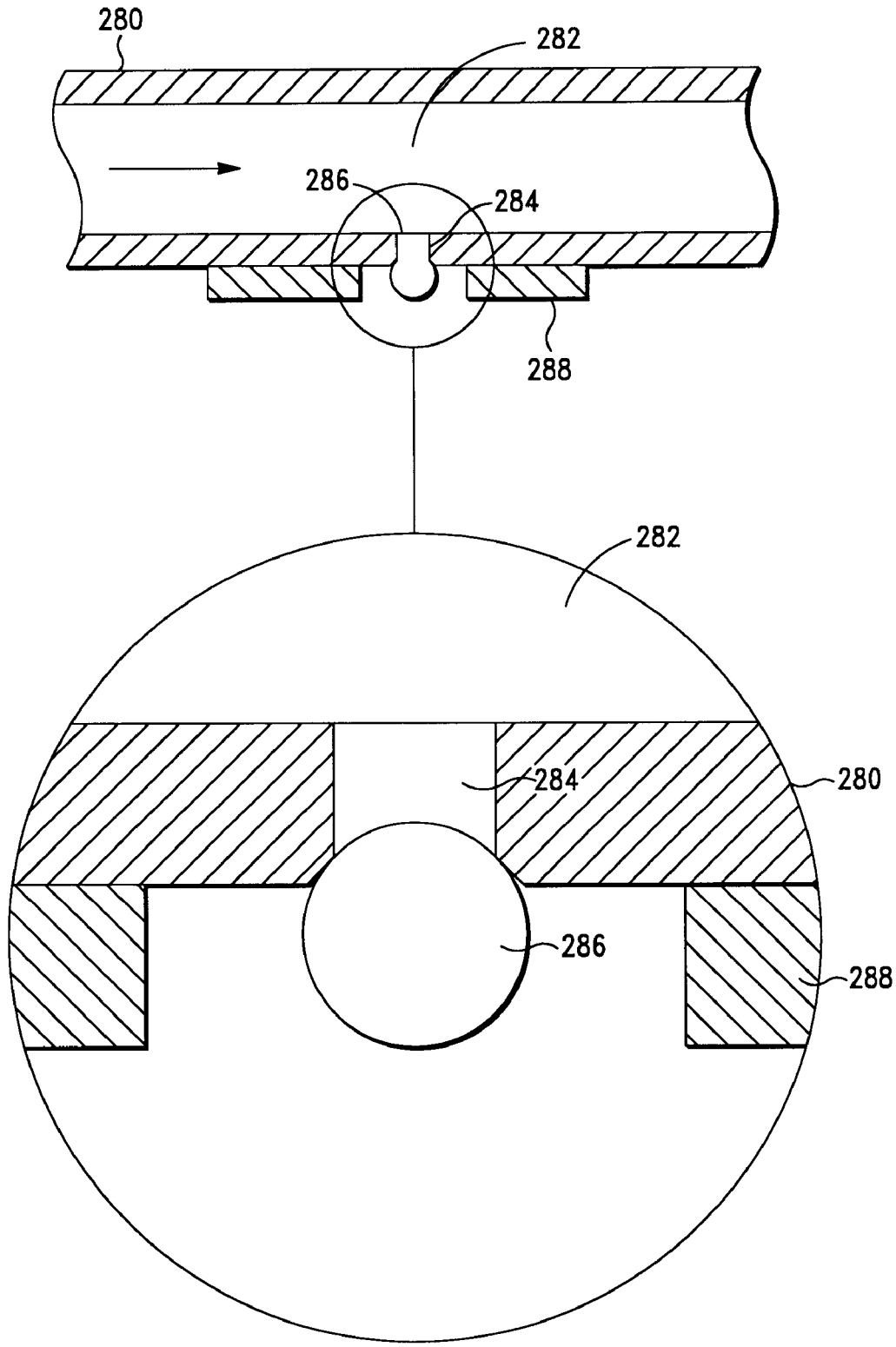
FIG. 14 is a cross-sectional view of an alternate dispenser tip with a piezo device for drop size control and an expanded view of the dispenser tip.

FIG. 14 is a cross-sectional view of an alternate dispenser tip with a piezo device for drop size control and an expanded view of the dispenser tip. The eluant inlet conduit 280 through which the eluant containing the sample fractions flows, leads to an ejection chamber 282. Drop ejection outlet passageway 284 communicates with the ejection chamber 282 to form a droplet 286 in the outlet end thereof. A piezo-electric vibrator 288 surrounds the outlet 284 to send vibrations to the passageway 284 and droplet 286 to effect release of smaller droplets from the passageway 284. The voltage to the piezo-electric unit is supplied by a variable frequency alternator or power supply or an equivalent voltage frequency control device (not shown).

Figure 15:
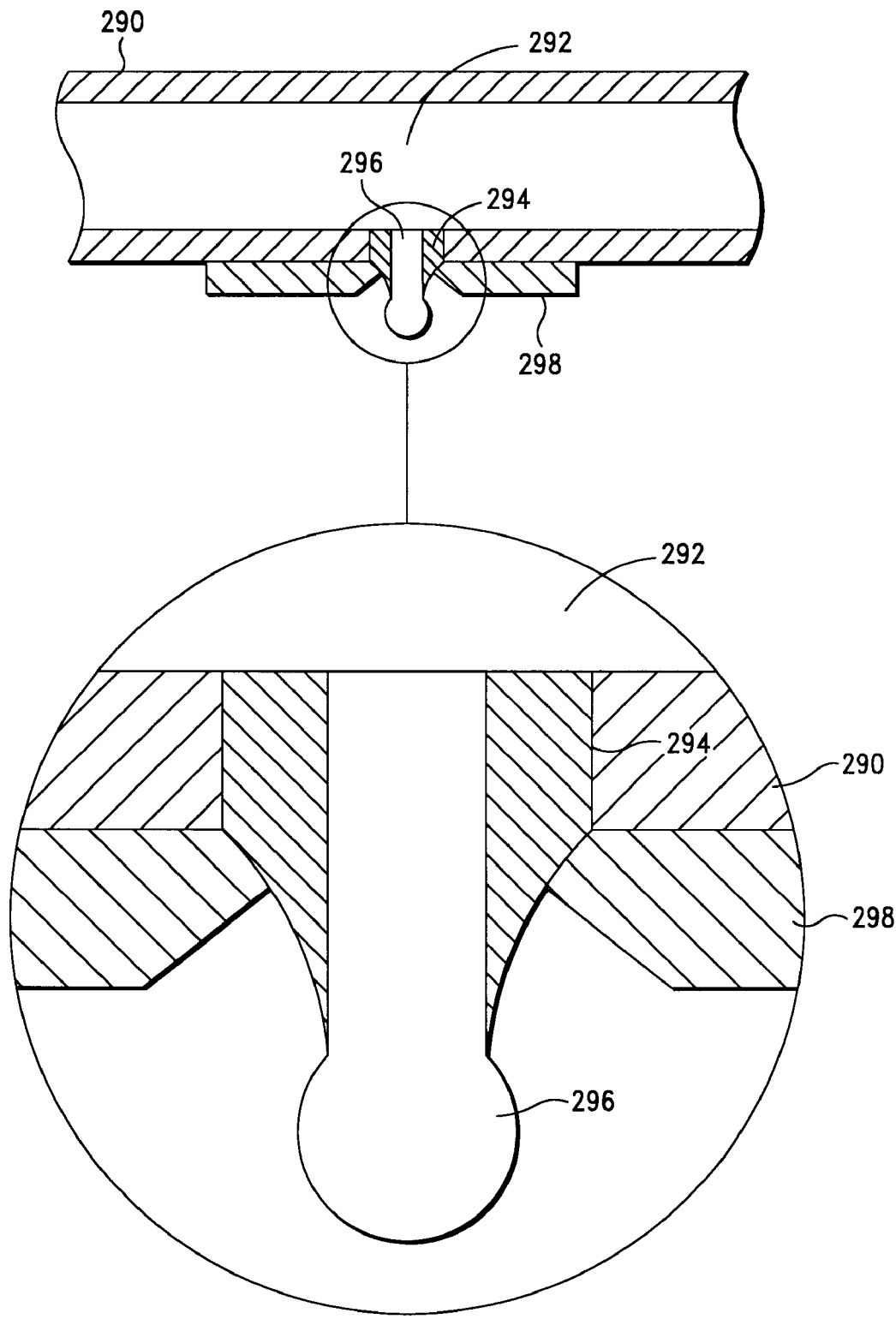
FIG. 15 is a cross-sectional view of an alternate dispenser tip with a nozzle and piezo device combination for drop size control and an expanded view of the dispenser tip.

FIG. 15 is a cross-sectional view of an alternate dispenser tip with a nozzle and piezo device combination for drop size control and an expanded view of the dispenser tip. The eluant inlet conduit 290 through which the eluant containing the sample fractions flows, leads to an ejection chamber 292. Drop ejection outlet nozzle 294 communicates with the ejection chamber 292 to form a droplet 296 in the outlet end thereof. A piezo-electric vibrator 298 surrounds the outlet nozzle 294 to send vibrations to the nozzle 294 and droplet 296 to effect release of smaller droplets from the nozzle 294. The voltage to the piezo-electric unit is supplied by a variable frequency alternator or power supply or an equivalent voltage frequency control device (not shown).

Figure 16:
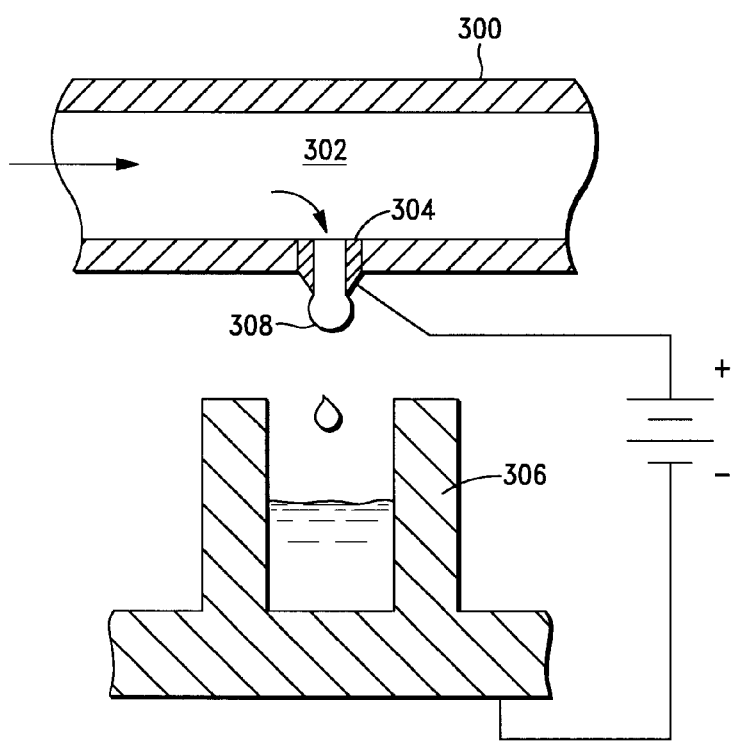
FIG. 16 is a cross-sectional view of an alternate dispenser tip with a combination of a nozzle and an electrostatic drop size control.

FIG. 16 is a cross-sectional view of an alternate dispenser tip with a combination of a nozzle and an electrostatic drop size control. An electrostatic droplet former is described in U.S. Pat. No. 5,639,467, the entire contents of which are hereby incorporated by reference. Eluant containing separated polynucleotide fractions is directed by conduit 300 to the ejection chamber 302 and therefrom to waste. The outlet nozzle 304 communicates with the ejection chamber 302. The outlet nozzle 304 is a conductive material which preferably will not contribute multivalent cations to the solution. Titanium is a preferred material. A positive voltage is supplied to the outlet nozzle 304. The sample collection vial 306 is connected to ground or is positioned on a grounded plate (not shown) so that a voltage difference is established between the nozzle 304 and droplets 308, and the vial 306. The voltage difference is preferably in the range of from 1 to 400 KV. Currents of from 0.2 $\mu$A to about 10 $\mu$A are acceptable. The voltage difference pulls the droplet free from the nozzle 304 while it is small. The size of the drop formed is a function of the voltage difference. It will be readily apparent to a person skilled in the art that same results can be obtained when reversing the polarity, and both are intended to be included within the scope of this invention.

Figure 17:
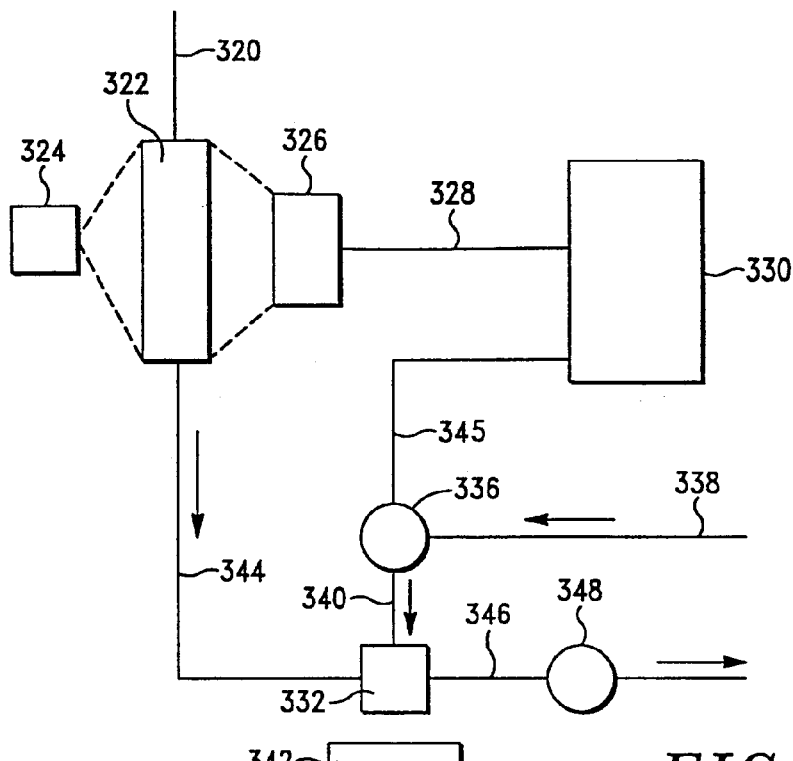
FIG. 17 is a schematic view of the combination of the detector, central controller and air puff drop size control system.

FIG. 17 is a schematic view of the combination of a conventional detector, a central controller and a drop size control system of this invention. The eluant stream containing the polynucleotide fractions passes through conduit 320 to the detection cell 322. A light source 324 directs light through the cell 322. Light emitted from the cell is collected and measured by the detector 326, producing an outlet voltage which is a function of the strength of the light emission at the selected emission frequency. UV light having a wavelength of 268 nm is conventionally used for polynucleotide level measurements. If the polynucleotides have a fluorescent moiety bound thereto, the detector can be a fluorescent detector which measures the emissions at a wavelength which matches the principal emission wavelength of the fluorescent moiety.

The output voltage signal from the detector 326 is fed by line 328 to the central controller unit 330 where the signal is amplified and analyzed.

The eluant stream exiting the measurement cell 322 is directed to the drop former 332 by the conduit 334. In this embodiment, the drop former 332 can be an air puff system shown in greater detail in FIGS. 8, 9 and 10, for example. The ejection chamber of the drop former 332 is supplied with air puffs from the puff valve 336 which received compressed gas through conduit 338. The air puffs are fed to the ejection chamber through air puff conduit 340 communicating with the puff valve 336 and the ejection chamber 332 to form fraction droplets which are collected in sample containers in plate 342.

The puff valve 336 opens in response to an open valve signal from the controller 330 through line 345.

The eluant remaining after drop formation is fed to waste through conduit 346, which includes a restriction valve 348.

Figure 18:
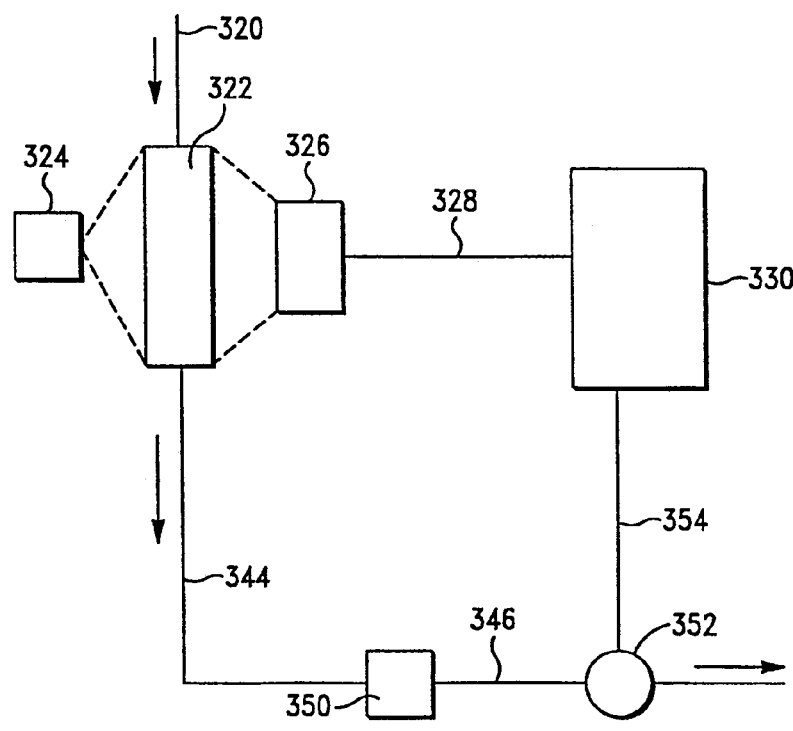
FIG. 18 is a schematic view of the combination of the detector, central controller and flow restriction control system.

FIG. 18 is a schematic view of the combination of the detector, central controller and flow restriction control system. The schematic representation in FIG. 18 has many of the same elements as the schematic representation in 30 FIG. 17, and where the same number are used in both views for the same elements. The drop former 350 can be the same as described in any of FIGS. 11–16. The restriction means 352 includes a restriction activator which responds to a activate restriction command through line 354 from the central controller 330, thereby increasing the pressure in the ejection chamber. Referring to FIG. 11, the increased pressure required is sufficient to overcome the interfacial tension of the liquid in the ejection chamber 222 and cause liquid to flow through the capillary-size opening 230.

Figure 19:
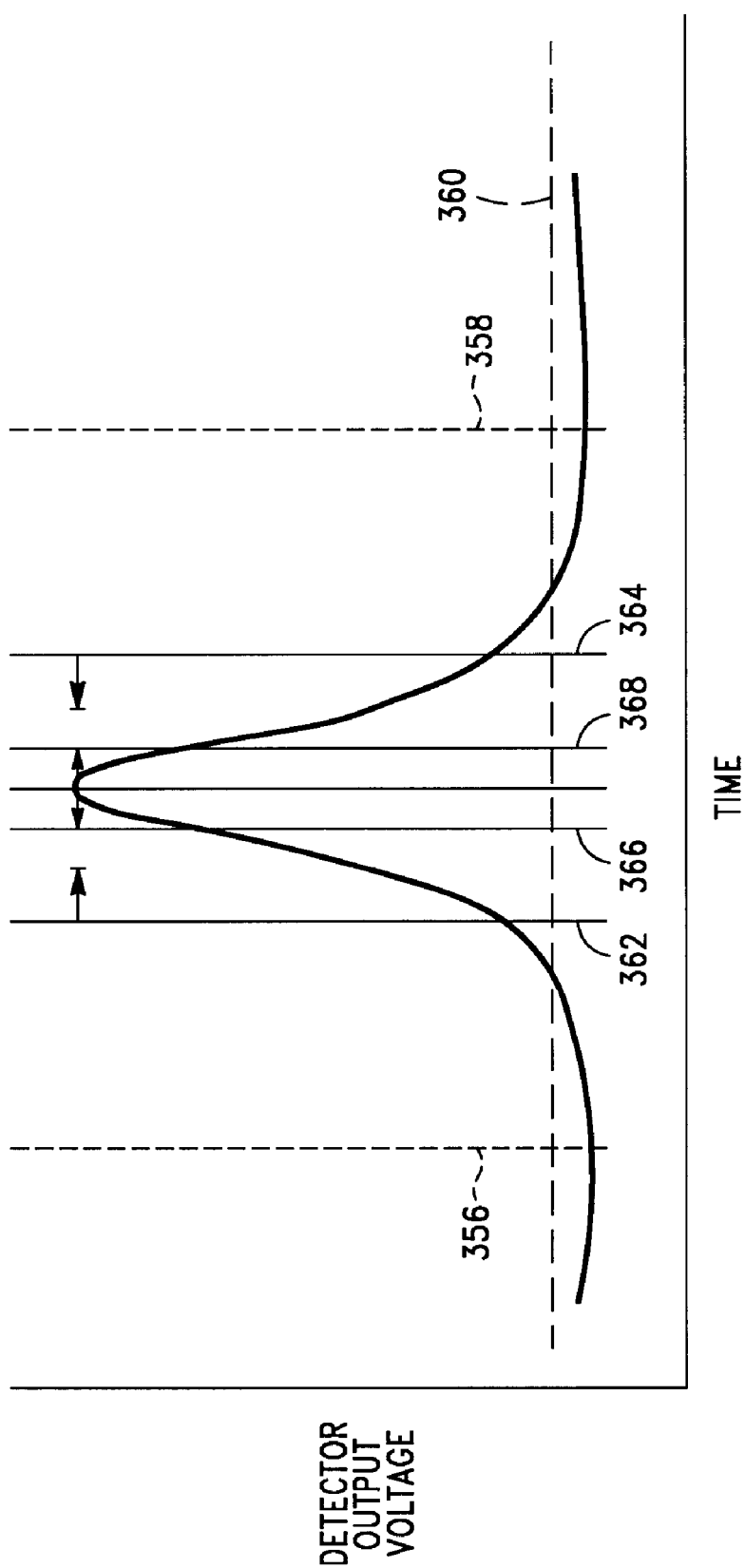
FIG. 19 is a representation of a chromatogram illustrating criteria for fraction collection based on time interval, threshold and slope.

FIG. 19 is a representation of a chromatogram illustrating criteria for fraction collection based on time interval, threshold and slope. A fraction is collected by opening the puff valve 178 shown in FIG. 8 or closing a flow restriction 234 as shown in FIG. 11 or both if both are provided in a system.

The open puff valve or close restriction commands can be sent to the respective collection activators during a time window with or without confirmation of the presence of a peak indicating the presence of a fraction. In other words, the collection can be made blind at a selected time window (shown by the vertical lines 356 and 358) which is known to contain a target polynucleotide, if the polynucleotide is present. This is particularly useful if the sample contains only a trace quantity of a desired base-pair length fraction of a polynucleotide. This method collects the widest fraction range, and the product may include portions of another fractions.

Alternatively, the open puff valve or close restriction commands can be sent to the respective collection activators during an interval when the detector signal is above an absolute threshold value shown by the broken line 360. This method collects a narrower fraction range, eliminating other fractions if the peak is distinct. However, if the peak is not clearly defined, other fractions may be included in the sample collected.

In a third alternative, the open puff valve or close restriction commands can be sent to the respective collection activators during an interval when the slope of the leading edge is above a certain selected value and when negative of the trailing edge is above a selected value. The slope values can be selected to collect most of the fraction by selecting lower slope values (shown by the vertical lines 362 and 364). Alternatively, the slope values can be selected to be a higher value (shown by the vertical lines 366 and 368) in order to collect only the central, purest portion of the fraction.

The controller 330 receives instructions identifying the position of the vial or well where the next collection should be conducted. It can receive specific X-Y coordinates of the vial or, it can receive a tray number, tray type, row number, and column number. It also receives the vial volume and can interrupt the collection when the vial can overflow.

The controller 330 receives a transit time for the apparatus. This is the travel time of a screened sample from the detector 326 to the ejection chamber. Based on this data, the controller can activate the air puff valve at the precise time that the detected fraction or a portion of a fraction reaches the ejection chamber.

The controller 330 receives instructions on a time frame of the collection. In case of blind collection, the instructions will be in the form of specific times to begin and to end collection for a specific fraction or a start time and a length of collection interval. A confirmation of the presence of the actual peak from the detector 326 is not required.

For Threshold Collection, the controller 330 receives the level of intensity generated by the UV detector 326 at which collection should start. When the level of intensity falls below this threshold or the vial specified for the collection of this fragment is full, the controller gives the puff valve a command to terminate collection.

For Slope Collection, the controller 330 receives a Slope Threshold, i.e., the rate of growth of the intensity generated by the UV detector 326 at which the collection should begin. When the slope of the curve exceeds a specified threshold, the controller 330 gives the puff valve 336 an instruction to start collection. The collection can be interrupted at any point if the vial specified for the collection of the fragment is full. Otherwise the collection proceeds when the slope turns negative, i.e. passes the peak value of the intensity. The collection is interrupted when the absolute value of the slope of the curve falls below the specified level.

The controller 330 gives the following commands to the fragment collector system.

The controller 330 commands the X and Y movements of the fragment dispenser 114 by commands to the stepper motors 134 and 156. The controller commands the Z movement of the fragment dispenser by commands to the dispenser support carriage 116.

The controller 330 commands the on/off status of the puff valve 336 which precipitates discharge of the passing sample liquid into the chosen well.

The controller 330 can command the fragment dispenser 114 to move to rinse position and then turn on a rinsing pump.

The controller 330 can regulate the level at which the puff valve is open and thereby control the flow rate of the sample being collected. By controlling the speed of sample flow, shear force damage to the collected polynucleotide fragments can be prevented.

The controller 330 can control the puff valve 336 to collect a single drop.

The invention claimed is:

1. A system for separating an aqueous stream of mixed polynucleotides into a series of length-based polynucleotide fractions and collecting one or more of the length-based polynucleotide fractions into separate containers comprising:
 a separation column containing separation media for separating an aqueous stream of mixed polynucleotides into a series of length-based polynucleotide fractions;
 container means including one or more single-sample containers;
 an ejection chamber having a separated sample inlet for receiving the length-based polynucleotide fractions, a waste outlet for discharging uncollected sample, and a capillary-sized fraction outlet positioned to discharge a selected length-based polynucleotide fraction into a single-sample container; and
 means for effecting discharge of a selected length-based polynucleotide fraction into the single-sample container wherein the means for effecting discharge of a selected length-based polynucleotide fraction into a single sample container includes a puff valve having a pressurized gas inlet and a puff gas outlet and wherein the ejection chamber includes a puff gas inlet communicating with the puff gas outlet, whereby activation of the puff valve will discharge a puff of gas into the ejection chamber and will effect discharge of sample through the fraction outlet,
 wherein the means for effecting discharge of a selected length-based polynucleotide fraction into the single-sample container includes a flow restriction actuator, a flow restriction in the waste conduit which will restrict flow of uncollected sample upon actuation by the flow restriction actuator, whereby actuation of the flow restriction will effect an increase in liquid pressure in the ejection chamber.

2. A system of claim 1 wherein the actuation of the flow restriction effects discharge of sample through the fraction outlet.

3. A system of claim 2 including computer control means for effecting discharge of the length-based polynucleotide fractions by actuation of the flow restriction.

4. A system of claim 1 including computer control means for effecting discharge of the length-based polynucleotide fractions by opening the air-puff valve.

5. A system of claim 1 wherein the fraction outlet has an outlet opening, and the outlet opening is combined with drop size reduction means for reducing the size of droplets discharged into the sample container, wherein the drop size reduction means is a gas-knife surrounding the fraction outlet and positioned to dislodge fluid through the outlet opening in the form of small droplets.

6. A system of claim 1 wherein the fraction outlet has an outlet opening, and the outlet opening is combined with drop size reduction means for reducing the size of droplets discharged into the sample container, wherein the drop size reduction means is a piezo-electric vibrator.

7. A system of claim 1 wherein the fraction outlet has an outlet opening, and the outlet opening is combined with drop size reduction means for reducing the size of droplets discharged into the sample container, wherein the drop size reduction means is an electrostatic separator.

8. A system of claim 1 wherein the fraction outlet has an outlet opening, and the outlet opening is combined with drop size reduction means for reducing the size of droplets discharged into the sample container, wherein the drop size reduction means is a nozzle having a small orifice having a gas-knife surrounding the nozzle and positioned to dislodge fluid through the outlet opening in the form of small droplets.

9. A system of claim 1 wherein the fraction outlet has an outlet opening, and the outlet opening is combined with drop size reduction means for reducing the size of droplets discharged into the sample container, wherein the drop size reduction means is a nozzle having a small orifice having a piezo-electric vibrator positioned adjacent to the nozzle.

10. A system of claim 1 wherein the fraction outlet has an outlet opening, and the outlet opening is combined with drop size reduction means for reducing the size of droplets discharged into the sample container, wherein the drop size reduction means is a nozzle having a small orifice having an electrostatic separator, and the nozzle has a charge opposite to the charge of the sample container.

11. A system of claim 1 for separating an aqueous stream of mixed polynucleotides into a series of length-based polynucleotide fractions and collecting one or more of the length-based polynucleotide fractions into separate single-fraction containers, the system including computer control means for controlling the means for effecting discharge of the length-based polynucleotide fractions.

12. A system of claim 11 wherein the computer control means includes a means for responding to a fraction detector output signal to determine the time interval for effecting discharge of a length-base fraction.

13. A system of claim 11 wherein the computer control means includes a means for responding to a fraction detector output signal to determine when the signal strength exceeds a threshold value to determine the time interval for effecting discharge of a length-base fraction.

14. A system of claim 11 wherein the computer control means includes a means for responding to a fraction detector output signal to determine when the signal slope exceeds a preset value to determine the time interval for beginning discharge of a length-base fraction.

* * * * *